(12) United States Patent
Jackson (10) Patent No.: US 6,454,807 B1
(45) Date of Patent: Sep. 24, 2002

(54) ARTICULATED EXPANDABLE SPINAL FUSION CAGE SYSTEM

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 14 days.

(21) Appl. No.: 09/726,724

(22) Filed: Nov. 30, 2000

(51) Int. Cl.⁷ .................................................. A61F 2/44
(52) U.S. Cl. .................................................. 623/17.15
(58) Field of Search .......................... 623/17.11, 17.15, 623/17.16

(56) References Cited

U.S. PATENT DOCUMENTS

| | | | |
|---|---|---|---|
| 5,015,255 A | | 5/1991 | Kuslich |
| 5,059,193 A | | 10/1991 | Kuslich |
| 5,263,953 A | | 11/1993 | Bagby |
| 5,458,638 A | | 10/1995 | Kuslich et al. |
| 5,489,307 A | | 2/1996 | Kuslich et al. |
| 5,489,308 A | | 2/1996 | Kuslich et al. |
| 5,554,191 A | * | 9/1996 | Lahille et al. ............ 623/17.11 |
| 5,593,409 A | | 1/1997 | Michelson |
| 5,609,636 A | | 3/1997 | Kohrs et al. |
| 5,653,763 A | * | 8/1997 | Errico et al. ............. 623/17.11 |
| 5,658,336 A | * | 8/1997 | Pisharodi ................ 623/17.11 |
| 5,658,337 A | | 8/1997 | Kohrs et al. |
| 5,683,391 A | | 11/1997 | Boyd |
| 5,782,832 A | | 7/1998 | Larsen et al. |
| 5,797,909 A | | 8/1998 | Michelson |
| 5,885,287 A | | 3/1999 | Bagby |
| 6,080,193 A | * | 6/2000 | Hochshuler et al. ..... 623/17.11 |
| 6,129,763 A | * | 10/2000 | Chauvin et al. ......... 623/17.11 |
| 6,159,244 A | * | 12/2000 | Suddaby ................... 623/17.11 |
| 6,159,245 A | * | 12/2000 | Meriwether et al. ..... 623/17.11 |
| 6,179,875 B1 | * | 1/2001 | Von Stremple .......... 623/17.16 |
| 6,183,517 B1 | * | 2/2001 | Suddaby ................... 623/17.16 |
| 6,193,757 B1 | * | 2/2001 | Foley et al. ............. 623/17.16 |
| 6,231,609 B1 | * | 5/2001 | Mehdizadeh ............. 623/17.11 |
| 6,332,895 B1 | * | 12/2001 | Suddaby ................... 623/17.11 |

* cited by examiner

Primary Examiner—David H. Willse
Assistant Examiner—Suzette J. Jackson
(74) Attorney, Agent, or Firm—Shughart Thomson & Kilroy P.C.; Marcia J. Rodgers

(57) ABSTRACT

An apparatus and method for implanting an articulated spinal fusion cage into the intervertebral space and adjusting the cage in situ to support the adjacent vertebrae in a normal curved alignment. The invention provides a greatly improved modular cage system having a base unit with a pair of sockets for receiving the ends of a pair of legs. The sockets permit pivotal movement of the legs about a posterior fulcrum from a closed, parallel insertion position to an anteriorly open, wedge-shaped orientation. The base has a threaded bore for receiving a driver, which is operable to urge the anterior ends of the legs apart as well as to support the front of the installed fusion cage. Interchangeable drivers are provided having various sized tips. The interior end surface of each leg unit includes a driver-receiving groove for providing torsional stability. Alternatively, a pair of pins and bores are provided on the inner surfaces of the opposed ends for receiving a driver tip. In certain embodiments the base is of integral construction with one of the legs, and includes a socket for receiving a pivot end of the second leg.

20 Claims, 4 Drawing Sheets

ARTICULATED EXPANDABLE SPINAL FUSION CAGE SYSTEM

The present invention is broadly concerned with a spinal fusion cage system. More particularly, it is directed to an articulated implant which can be selectively anteriorly expanded in situ to form a wedge with an adjustable angle of inclination for supporting adjacent vertebrae in normal curved alignment.

The spine is a column of stacked vertebrae which are normally axially aligned along the median plane. Thus, when viewed from the front or back the spine appears to be straight. When viewed from a lateral perspective, however, the spine is shown to be comprised of four distinct curves. Each vertebra is angularly displaced in the coronal plane in accordance with its position along one of the respective curves.

The structure of each vertebrae includes a rounded, weight bearing anterior element, or vertebral body, which is separated from the adjacent superior and inferior vertebral bodies by fibrocartilage pads or discs. These intervertebral discs support the adjacent vertebrae in an appropriate angular orientation within a respective spinal curve and impart flexibility to the spine so that it can flex and bend yet return to its original compound curvate configuration.

When aging, injury or disease cause damage to the discs or to the vertebrae themselves, it may be necessary to surgically remove a disc and fuse the adjacent vertebral bodies into a single unit. Such surgical arthrodesis is generally accomplished by implanting a cage-like device in the intervertebral space. The cages are apertured, and include a hollow interior chamber which is packed with live bone chips, one or more gene therapy products, such as bone morphogenic protein, cells that have undergone transduction to produce such a protein, or other suitable bone substitute. Following implantation, bone from the adjacent vertebrae eventually grows through the apertures and fuses with the bone of the adjacent vertebrae above and below the cage, thus fixing the adjacent bones as well as the cage in position.

Once the disc has been removed from the intervertebral space, the angular orientation of the adjacent vertebrae is established and stabilized by the three dimensional geometry of the implanted fusion cage, and the vertebrae will eventually fuse in this orientation. The cervical and lumbar curves each present a region of normal anterior convexity and posterior concavity or lordosis. There is a need for a posterior implant for use in these regions, and in particular in the lumbar region, which can be adjusted in situ to achieve and maintain normal lordosis of the vertebrae.

Previous attempts to achieve normal spinal curvature with fusion cages have involved trial insertion of cages of various different sizes into the intervertebral space, removal of the cage and replacement with another until an optimal angular incline is achieved. There is a need for a modular and articulated implant which can be installed between the vertebrae in a first configuration, and adjusted in situ into a wedge configuration. It is also preferable that the bearing surfaces of the device be supported at both the anterior and the posterior end, so that neither end of the device is left unsupported following angular adjustment.

Once installed in an intervertebral space, a spinal implant may be subject to twisting forces caused by unequal lateral distribution of weight on the adjacent vertebral bodies. This may occur, for example, during normal bending and reaching activity. There is also a need for an implant which will provide torsional stability to resist such twisting forces.

The apparatus of the present invention is specifically designed to provide a modular intervertebral implant which can be selectively expanded anteriorly in situ to form a wedge which stabilizes the adjacent vertebrae in normal curved alignment without loss of torsional stability.

SUMMARY OF THE INVENTION

The present invention is directed to an apparatus and method for implanting an articulated modular cage in the intervertebral space and adjusting it in situ to support the adjacent vertebrae in a normal curved alignment while permitting fusion of the adjacent bones. The fusion cage system of the present invention includes a base unit having a pair of sockets for receiving a pair of corresponding legs. The sockets permit pivotal movement of the legs about a posterior fulcrum from a closed, parallel insertion position to an anteriorly open, wedge-shaped orientation which may be selectively adjusted to provide appropriate angular support. The base also includes a threaded bore for receiving a wedge or driver. The driver is inserted through the bore and is operable to urge the opposed anterior ends of the legs apart while pivoting the posterior ends within their respective sockets. A plurality of drivers having elongate shafts with tips of various diameters is provided. A driver is selected and advanced between the opposed ends of the legs to support the legs in a predetermined angular orientation. Preferably, each leg unit includes a driver-receiving groove on the inner surface of the opposed end for providing torsional stability. Pins may also be employed to impart torsional stability. Alternatively, the base may be of integral construction with one of the legs, and may include a socket for receiving and permitting pivotal rotation of the second leg to form a wedge.

OBJECTS AND ADVANTAGES OF THE INVENTION

The principal objects of the present invention are: to provide an improved apparatus and method for fusing together adjacent vertebrae; to provide such an apparatus and method for introducing a bone graft between adjacent vertebrae; to provide such an apparatus and method for intervertebral implantation while maintaining or correcting the angular alignment of the vertebrae of the spine; to provide such an apparatus and method for implanting a dual cage system; to provide such an apparatus and method for adjustment of the alignment and balance of the spine in situ; to provide such an apparatus having an intervertebral cage which can be selectively anteriorly expanded to form a wedge with an adjustable angle of inclination; to provide such an apparatus having two such independently adjustable intervertebral cages; to provide such an apparatus having a modular intervertebral cage system; to provide such an apparatus having an articulated intervertebral cage; to provide such an apparatus having a pair of legs and a base permitting articulated movement of one or both of the legs about a posterior fulcrum from a closed, parallel insertion position to an anteriorly open, wedge-shaped orientation; to provide such an apparatus having an array of drivers with tips of various diameters that each provides a different degree of expansion to allow for variation in the angular configuration between the top and bottom of the cage for adjustment of the angle of curvature between two vertebral bodies; to provide such an apparatus having an intervertebral cage including structure providing torsional stability; to provide such an apparatus having a groove on the inner anterior surface of the leg for receiving and retaining the tip of a driver; to provide such an apparatus having a pair of pins coupled with the anterior bearing surface of one of the legs for adjustable registry with a pair of corresponding apertures on the second leg; to provide such a fusion cage which includes an interior chamber for supporting a bone graft; to provide such a fusion cage which is apertured to permit outgrowth of a bone graft into the surrounding vertebrae; to provide a method for using such an apparatus for implanting a cage unit between two adjacent vertebral bodies, packing the cage unit with a bone graft, adjustably coupling the cage unit with a driver for forming the cage unit into a wedge having a predetermined angle between top and bottom surfaces thereof, and permitting the bone graft to grow and fuse the adjacent vertebral bodies together; providing such an apparatus and method which are relatively easy to use, inexpensive to produce and particularly well-suited for their intended usage.

Other objects and advantages of this invention will become apparent from the following description taken in conjunction with the accompanying drawings wherein are set forth, by way of illustration and example, certain embodiments of the invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figures 4, 5:
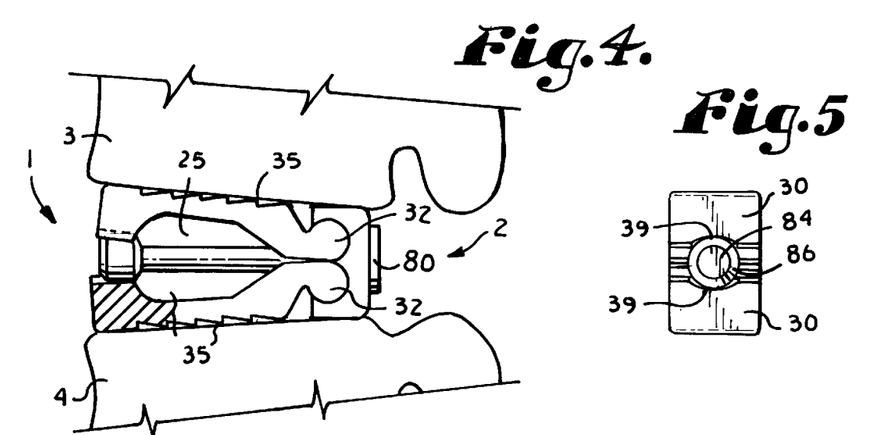
FIG. 4 is a side perspective view of the cage of FIG. 2 installed between adjacent vertebrae, with portions of the lower leg broken away to illustrate position of the driver tip within the groove when the driver is fully advanced.
FIG. 5 is a front perspective view of the apparatus depicted in FIG. 4.
Figure 6:
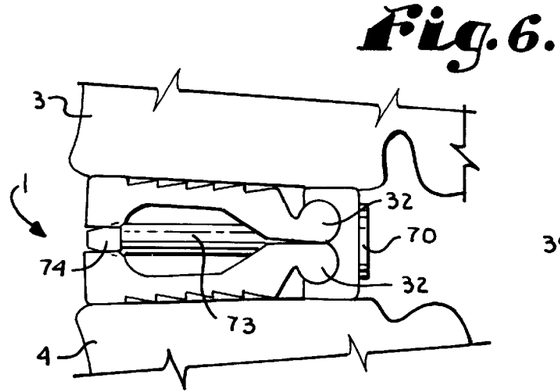
FIG. 6 is a side perspective view similar to FIG. 4, illustrating a driver having a conical tip.

Referring now to the drawings, an articulated expandable spinal fusion cage system in accordance with the invention is generally indicated by the reference numeral 1 and is depicted in FIGS. 1–7. FIG. 4 illustrates a partial side view of a human spine showing the intervertebral region 2, which is the functional location of implantation of the fusion cage system 1, between the vertebral bodies of selected upper and lower adjacent vertebrae 3 and 4.

Referring again to FIG. 1, the fusion cage system 1 broadly includes a first leg 10 and a second leg 11, which are adjustably coupled with a base 12 and retained in place by one of an assortment of drivers or inserts 13. The legs 10 and 11 are substantially identical, each having an anterior first end 20 and a posterior second end 21 interconnected by a central web portion 22. The anterior ends 20 of legs 10 and 11 may be displaced apart from each other in order to anteriorly expand the fusion cage system 1.

Figures 1, 2, 3:
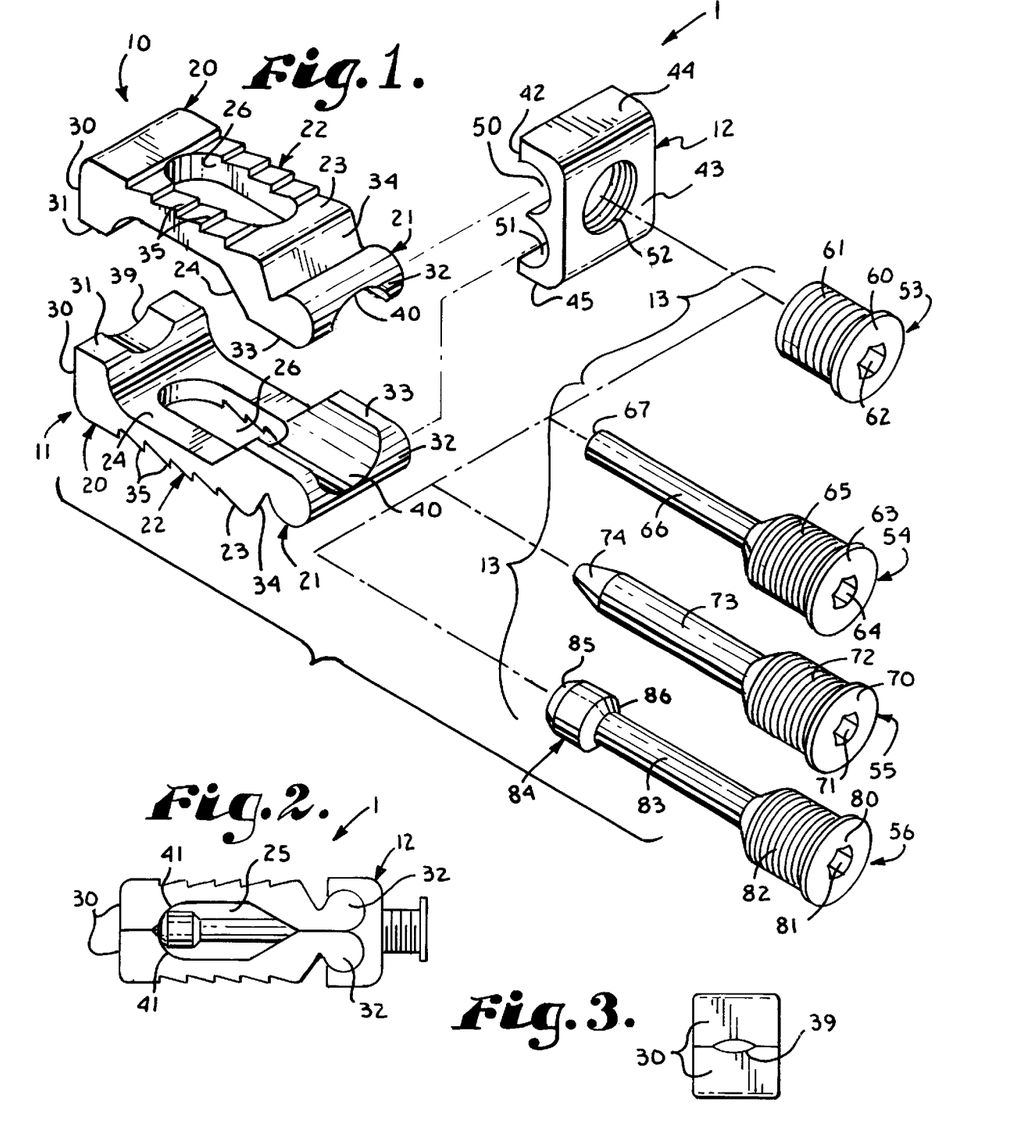
FIG. 1 is an exploded perspective view of an articulated expandable spinal fusion cage system in accordance with the present invention, illustrating an array of threaded drivers.
FIG. 2 is a side perspective view of the articulated spinal fusion cage of FIG. 1 showing installation of an adjusting driver with a radially expanded tip.
FIG. 3 is a front perspective view of the cage depicted in FIG. 2, showing a groove for receiving the tip of a driver.

The first end 20 and central web 22 of each leg 10 and 11 also include an outer, bone support surface 23 and an inner surface 24 defining an open-sided chamber 25 when the cage is assembled as depicted in FIG. 2. The central web portions 22 of the legs 10 and 11 are apertured by one or more radial ports or windows 26, which extend between the outer and inner surfaces 23 and 24 and open into the chamber 25.

The anterior end 20 of each leg 10 and 11 has a generally rectangular overall configuration, including an anterior face 30 orthogonally coupled with a bearing surface 31. The posterior end 21 of each leg 10 and 11 has a generally cylindrical overall configuration, including a pivot portion 32. When viewed from the side (FIG. 2), the pivot portion 32 is truncated along one side to form a relief surface 33. A groove 34 defines the juncture of the posterior end and central web portion 22 of each leg 10 and 11.

The outer support surface 23 of the central portion 22 includes a series of serrations or teeth 35. The teeth 35 serve to engage the surface of a respective adjacent vertebra 3 or 4 against slippage along an anterior-posterior axis within the intervertebral joint 2.

The leg inner surface 24 is generally smooth. The bearing surfaces 31 at the anterior end 20 and relief surface 33 at the posterior end 21 of each leg 10 and 11 are generally planar for engagement with the corresponding surfaces of the opposed leg 11 and 10. The bearing surfaces 31 of legs 10 and 11 are axially grooved so that, when the cage system 1 is assembled, the mating surfaces 31 cooperatively form an anterior channel 39, as best shown in FIG. 3. The relief surfaces 33 are axially grooved in like manner to form a posterior channel 40. The anterior and posterior channels 39 and 40 are adapted for sliding reception of a driver or insert 13. The inner surface of the chamber 25 is curved at the anterior aspect to form a cam surface 41.

The base 12 has a generally truncate cubic overall configuration that is approximately M-shaped when viewed from the side (FIG. 2). The base includes anterior and posterior faces 42 and 43 and top and bottom walls 44 and 45. The anterior face 42 is configured to include a pair of side-by-side receiver sockets 50 and 51, which are sized and shaped to receive the pivot portions 32 of the legs 10 and 11. A central threaded bore 52 extends between the anterior and posterior faces 42 and 43 for receiving one of an array of drivers or inserts 13.

Four exemplary inserts or drivers 53, 54, 55 and 56 are depicted in FIG. 1, although it is foreseen that the insert may have a wide variety of configurations. A first exemplary plug type insert 53 includes a radially expanded head 60 and a short threaded shank 61. The shank 61 is sized, shaped and threaded for operable reception within matingly threaded bore 52 and posterior channel 40, with the radially expanded driver head 60 snugged against the posterior face of the base 43. The driver head 60 includes a receiver 62 configured for reception of a driving tool such as a wrench (not shown). It is foreseen that the receiver may be configured to receive driving tools having a wide range of geometric shapes.

A second exemplary post-type driver 54 includes a similar head 63 with a central receiver 64, a short threaded shank 65 coupled with an elongate, unthreaded smooth shaft portion 66, which terminates in a truncated, plane surface tip 67. The driver 54 is sized to extend anteriorly through the posterior channel 40 for driving registry within the anterior leg channel 39. A third exemplary taper-type driver type 55 also includes a radially expanded head 70 with a central receiver 71, and a short threaded shank 72 coupled with an elongate, smooth shaft portion 73, which terminates in a tapered tip 74. A fourth exemplary bulb-type driver 56 also includes a head 80 having a central receiver 81, a short threaded shank 82 coupled with an elongate, smooth shaft 83, and terminating in a bulbous tip 84. The tip 84 includes anterior and posterior radial chamfers 85 and 86.

The legs 10 and 11, base 12 and drivers or inserts 13 are constructed of carbon fiber, or of a strong, inert material having a modulus of elasticity such as a stainless steel or titanium alloy, or of porous tantalum or any other biocompatible material or combination of materials.

In use, the posterior surface of a selected intervertebral region 2 of the spine of a patient is surgically exposed. The soft tissues are separated, the disc space is distracted and the disc is removed, along with any bone spurs which may be present. The disc space is distracted to a predetermined height which serve to decompress any affected nerve roots and to permit preparation of the intervertebral region 2.

The fusion cage system is assembled by a user by aligning the pivot portions 32 of first and second legs 10 and 11 with corresponding receiver sockets 50 and 51 and sliding the pivots 32 into engagement with the respective sockets 50 and 51. Thus partially assembled, the fusion cage system of the invention 1 presents a closed, overall rectangular configuration, with the legs 10 and 11 in a parallel orientation so that the bearing surfaces 31 rest against each other, as depicted in FIGS. 2 and 3.

The device may be inserted by tapping directly into the distracted intervertebral region 2, or the vertebrae 3 and 4 may be predrilled to receive the cage system 1. Although a posterior approach is preferred, it is foreseen that an anterior or even later approach could also be employed.

Figure 7:
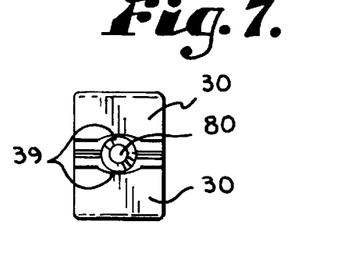
FIG. 7 is a front perspective view of the apparatus depicted in FIG. 6.

As best shown in FIGS. 2, 4, and 7, one of the array of drivers 13, for example plug 53, is selected and aligned with the threaded bore 52. The user positions a tool (not shown) in the receiver 62 in the plug head 60 and rotates the tool in a clockwise direction to drive the threaded shank 61 until it engages the bore 52. Installation of the plug 53 through the bore 52 and into the groove 40 prevents lateral shifting of the pivots 32 within the sockets 50 and 51. If plug 53 is selected, fully tightening the plug 53 in the bore 52 until the head 60 is snugged against the posterior face 43 of the base 12 will not alter the overall rectangular configuration of the fusion cage system 1 and the legs 10 and 11 will remain in parallel orientation.

If one of drivers 54–56 is selected, continued rotation of the tool will drive the smooth shaft 66, 73 or 83 through the chamber 25 bringing the plane surface tip 67, taper surface tip 74 or anterior chamfer 85 of the bulbous tip 84 into engagement with the cam surface 41. Continued rotation of the tool will cause the tip to advance forward, into the anterior channel 39, simultaneously wedging the bearing surfaces 31 apart and rotating the pivots 32 within the sockets 50, 51, so that the cage 1 begins to assume a generally wedge shape when viewed from the side.

In this manner, the angle formed by the outer, bone supporting surfaces 23 of the legs 10 and 11 is determined by the displacement of the bearing surfaces 31, which in turn is determined by the shape of the driver tip 64–66. The base module 12 is preselected in accordance with the vertical measurement of the intervertebral space 2. The driver is preselected to cause displacement of the legs 10 and 11 into an appropriate wedge shape which will support the adjacent vertebrae 3 and 4 at the proper height as well as the desired angular alignment to achieve normal curvature of the respective spinal region. Advantageously, registry of the pivot portions 32 within the sockets 50 and 51 and registry of the driver tip 64, 65, or 66 within the anterior channel 39 cooperatively support both the front and rear of the articulated fusion cage system 1 against both compression forces and torsional stresses.

If the first chosen driver 13 does not cause the desired angle of displacement when fully installed, then the tool is used to remove the driver 13 while leaving the legs and base 10, 11 and 12 installed in the intervertebral space 2. An alternate driver 13 is then selected and the process is repeated until the vertebrae 3 and 4 are supported by the cage system 1 in normal alignment.

The surgeon then transplants a quantity of packed bone cells or a suitable bone substitute material into the chamber 25 by a lateral approach through the open area between the first and second legs 10 and 11. Alternatively, the bone cells may be introduced into the chamber 25 by a posterior approach through the bore 52 prior to installation of the driver 13 or by a combination of these methods. Bone for use in the graft may be harvested from the patient as live bone, from a bone bank or from a cadaver. Demineralized bone matrix, bone morphogenic protein or any other suitable material may also be employed.

Following implantation, the bone grows between vertebrae 3 and 4, through the windows 26 with the bone in the chamber 25 and around the cage system 1 to fuse the bodies of vertebrae 3 and 4 together.

Those skilled in the art will appreciate that in addition to the method previously described the fusion cage system 1 may also be assembled and plug 53 installed prior to insertion of the cage system 1 into the intervertebral space 2. In addition, while an exemplary array of drivers 13 is depicted, an infinite variety of drivers 13, each producing a different degree of displacement of the legs 10 and 11 may be incorporated in the set to allow the surgeon to achieve a desired angle of displacement and consequent positioning of the vertebrae 3, 4 relative to each other. The driver tips are constructed of varying sizes and geometric configurations in order to provide an implant system 1 to allow a surgeon to first try a driver producing less expansion and then, if the surgeon finds that the expansion is insufficient to produce a normal angle of alignment between the adjacent vertebrae 3, and 4, to remove the first driver and insert one producing a greater angle of displacement of the legs 10 and 11. The process is repeated until the desigred alignment between the vertebrae is achieved. Inserts or drivers 53–56 are depicted in FIG. 1 as representative examples of a full range of possible sizes and geometric configurations.

The structure of a first modified embodiment of an articulated expandable spinal fusion cage system in accordance with the invention is shown in FIGS. 8–11 and is generally represented by the reference numeral 101. The system 101 is similar to the embodiment previously described, except that a system of pins and bores is employed to impart torsional stability.

In particular, the fusion cage system 101 includes first and second legs 102 and 103, a base 104 and an assortment of inserts, including a driver 110 having a bulbous tip 111, a driver 112 having a taper tip 113 and a post-type driver 114 having a truncate, planar tip 115. The legs 102 and 103 are of similar overall construction, each having an anterior first end 120, a posterior second end 121 and a central web portion 122. The legs each also include an outer support surface 123, and an inner surface 124 defining a chamber 125.

Figure 8:
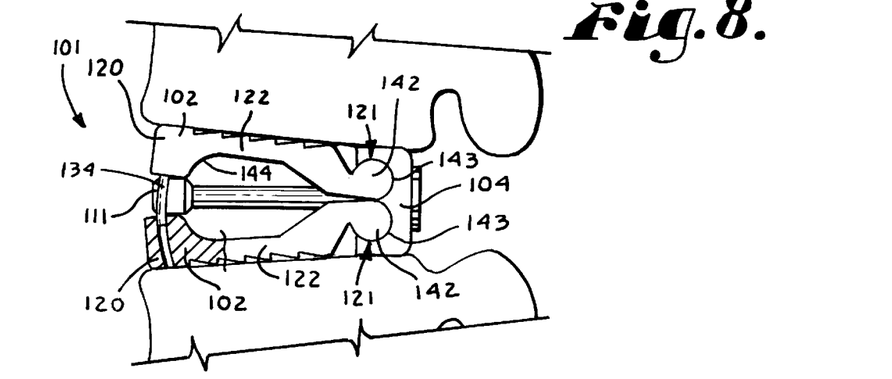
FIG. 8 is a side perspective view of a first modified embodiment of the invention installed between adjacent vertebrae, showing portions of the lower leg broken away to illustrate position of a pin within a slot after a driver is installed between the bearing surfaces of the legs.
Figure 9:
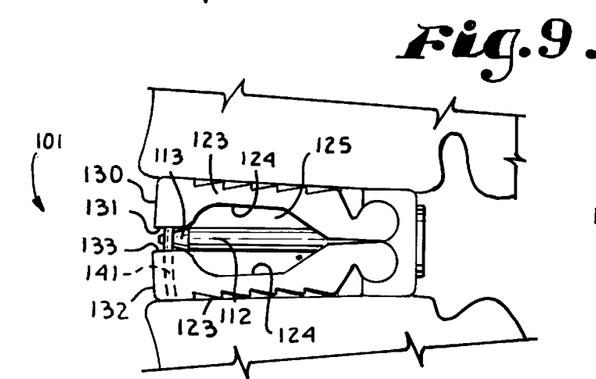
FIG. 9 is a side perspective view similar to FIG. 8, illustrating a driver having a conical tip, with the position of a pin shown in phantom.
Figure 10:
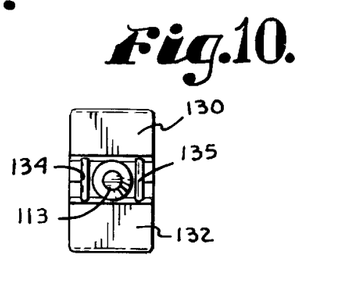
FIG. 10 is a front perspective view of the apparatus depicted in FIG. 9.
Figure 11:
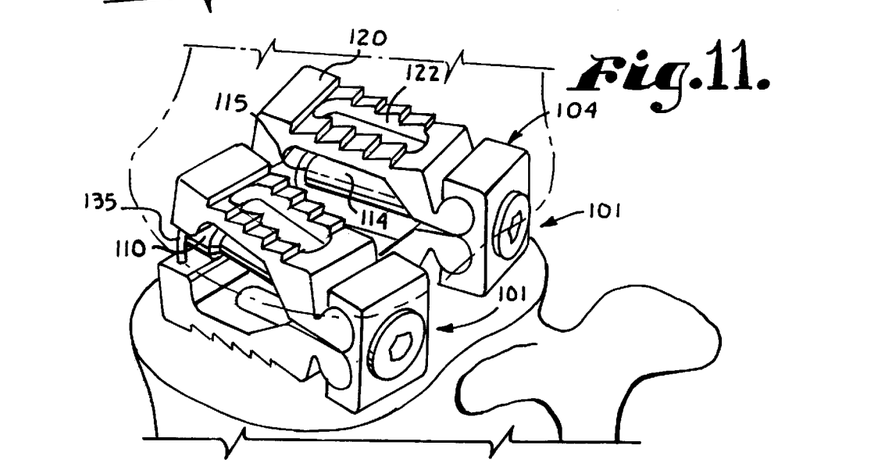
FIG. 11 is a perspective view taken from a superior left lateral-posterior position showing a pair of the cage systems of FIG. 8 installed between adjacent vertebrae, with the superior vertebrae shown in phantom.

The generally rectangular anterior end 120 of the first leg 102 includes anterior face 130 orthogonally coupled with a bearing surface 131. The corresponding anterior end 120 of the second leg 103 also includes an anterior face 132 coupled with a bearing surface 133. As best shown in FIG. 10, a pair of elongate curved pins 134, 135 project at spaced intervals from the bearing surface 131 of the first leg 102. As shown in FIGS. 8 and 9, bores 140 and 141 extend through the bearing surfaces 133 of the second leg 103 at intervals spaced to receive respective pins 134 and 135.

The posterior portion of the leg 121 is generally cylindrical and terminates in a pivot portion 142. The base 104 includes sockets 143 which are sized to receive the cylindrical pivot portions 142. The inner leg surfaces 124 are smooth and filleted at the anterior aspect of the chamber 125 to form a cam surface 144.

In use, the base 104 and legs 102 and 103 are assembled in a manner substantially similar to the embodiment previously described. The pins 134 an 135 are aligned in sliding engagement with the bores 140 and 141. The first ends 120 are urged together until the bearing surfaces 131 and 133 meet, causing the pins 134 and 135 to be fully received within the bores 140 and 141 and the cage system 101 to assume an overall rectangular configuration. The articulated fusion cage system 101 is implanted in the manner previously described. Upon installation, the tip 111, 113 or 115 of the driver 110-112 rides forwardly along the cam surface to the junction of the two planar bearing surfaces 131 and 133. The driver is urged forwardly until the tip 111, 113 or 115 rests between the pins 134 and 135 as depicted in FIGS. 8, 9 and 10. The registry of the pivot portions 142 within the sockets 143 and the extension of the pins 134 and 135 into bores 140 and 141 cooperatively support both the front and rear of the articulated fusion cage system 1 and prevent torsional movement of the legs.

Figures 12, 13, 14:
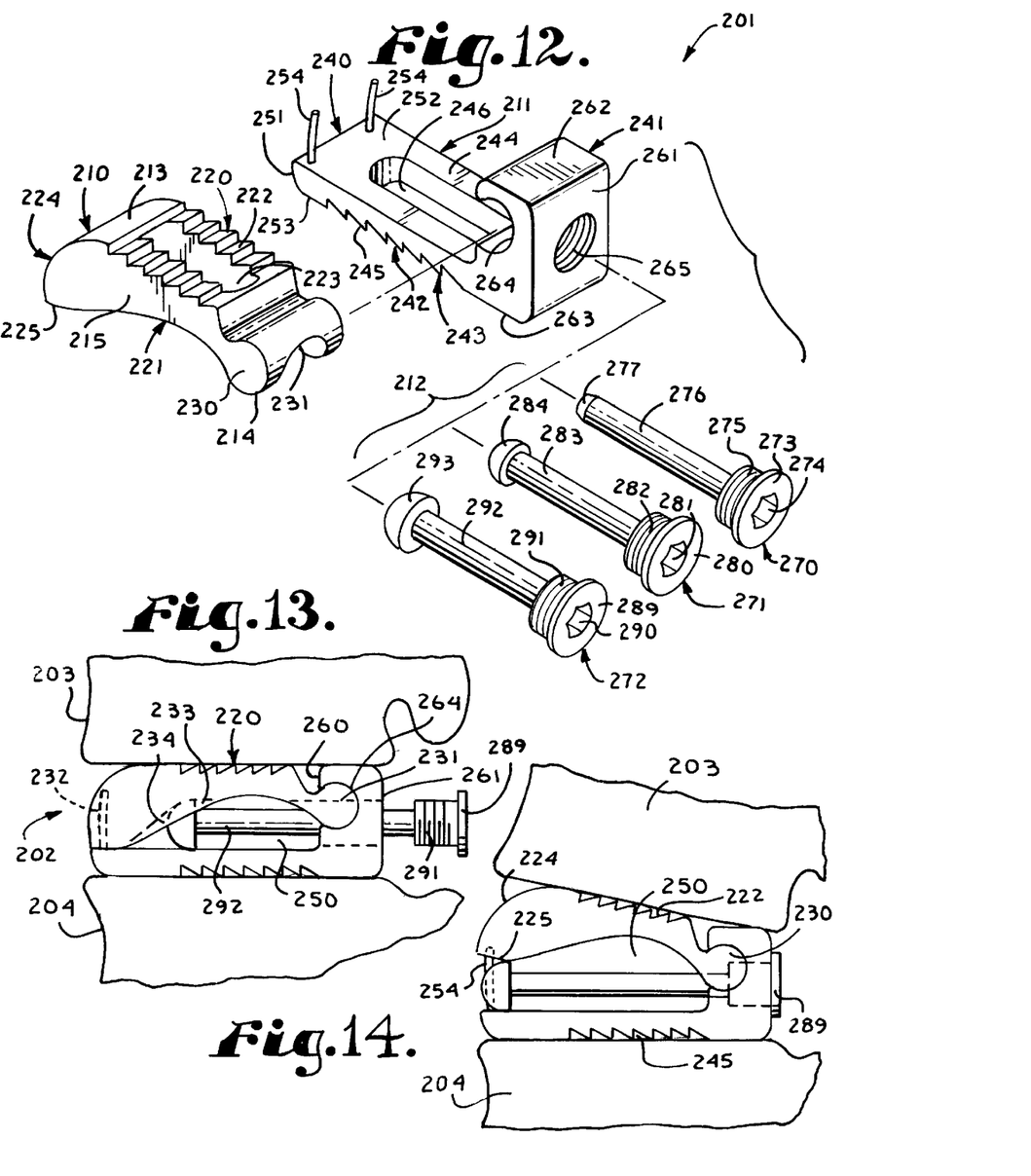
FIG. 12 is an exploded view of a second modified embodiment in accordance with the present invention, illustrating an array of threaded drivers.
FIG. 13 is a side perspective view of the cage of FIG. 12 installed between adjacent vertebrae, showing a bore and interior surfaces in phantom to illustrate the path of installation of a hemispherical headed driver.
FIG. 14 is a side perspective view of the apparatus of FIG. 13, with the driver installed between the bearing surfaces of the legs and the anterior portions of adjacent vertebrae displaced to achieve lordosis.

A second modified embodiment of an articulated expandable spinal fusion cage system in accordance with the invention is generally represented by the reference numeral 201 and is depicted in FIGS. 12–14. FIGS. 13 and 14 illustrate the system 201 installed in the intervertebral space 202 between adjacent upper and lower vertebrae 203 and 204.

The fusion cage system 201 broadly includes a first leg 210 and a second leg 211 which are intercoupled and retained in place by one of an assortment of drivers 212. The first leg 210 includes an anterior first end 213 and a posterior second end 214 intercoupled by a central web portion 215. The leg 210 also includes an upper, bone supporting surface 220 and an inner surface 221. The upper support surface 220 of the center web 215 includes a series of serrations or teeth 222 and the web is apertured by one or more radial ports or windows 223, which extend between the upper and inner surfaces 220 and 221.

The anterior end of the leg 213 has a generally elliptical configuration when viewed from the side, including a curvate anterior face 224 coupled with a generally planar bearing surface 225. The posterior end of the leg 214 has a generally cylindrical overall configuration, including a pivot portion 230. The lower portion of the pivot 230 is axially grooved to form a posterior channel 231.

The inner surface 221 of the leg 210 is relatively smooth. The bearing surface 225 is generally planar for bearing engagement with the corresponding surface of the second leg 211 and includes a pair of spaced bores 232. The inner surface 221 is axially grooved to form a central channel 233, the anterior aspect of which is filleted to form a cam surface 234 for a driver 212.

The second leg 211 also includes an anterior first end 240 and a posterior second end which is integral with a base 241, intercoupled by a central web portion 242. The leg 211 also includes a lower, bone supporting surface 243 and an inner surface 244. The lower support surface 243 of the center web 242 includes a series of serrations or teeth 245 and the web is apertured by one or more radial ports or windows 246, which extend between the lower and inner surfaces 243 and 244.

The first and second leg inner surfaces 221 and 244 define an open-sided chamber 250 when the cage is assembled as depicted in FIGS. 13 and 14. The windows 223 and 246 open into the chamber 250.

The anterior end of the leg 240 has a generally rectangular configuration, with an anterior face 251 intercoupling a generally planar upper bearing surface 252, and a bottom wall 253. A pair of spaced pins 254 project upwardly from the bearing surface 252 in spaced relationship for alignment with the upper leg bores 232. The posterior end of the leg or base 241 has a generally truncate cubic overall configuration that is eccentric when viewed from the side (FIG. 13). The base 241 includes anterior and posterior faces 260 and 261 and top and bottom walls 262 and 263. The anterior face 260 is configured to include a receiver or socket 264, sized and shaped to receive the pivot end 230 of the first leg 210. A central threaded bore 265 extends between the anterior and posterior faces 260 and 261 for receiving one of the array of drivers 212.

Three exemplary drivers 270, 271 and 272 are depicted in FIG. 12. A first exemplary tapered driver 270 includes a radially expanded head 273 with a central receiver 274, a short threaded shank 275, coupled with an elongate, unthreaded, smooth shaft portion 276, which terminates in a bevel tip 277.

A second exemplary hemi-tipped driver 272 includes a radially expanded head 280 with a central receiver 281, a short threaded thank 282 coupled with an elongate, smooth shaft portion 283, which terminates in a relatively small hemispherical tip 284.

A third exemplary hemi-tipped driver 289 is similar in construction to the second driver 271, including a head 229 with a central receiver 290, a short threaded shank 291 coupled with an elongate, smooth shaft 292, and terminating in a larger hemispherical tip 293.

In use, a second, lower leg 211 is selected having a posterior face 261 which approximately corresponds with the vertical measurement of the intervertebral space 20. The cage system 201 is assembled by aligning the end of the pivot portion 230 of the first leg 210 with the end of the lower leg socket 264 and positioning the first leg 210 so that the anterior end 213 clears the upstanding pins 254 on the lower leg 211. The pivot 230 slidingly engages the socket 264 and is urged laterally until it is fully supported within the socket 264. The pins 254 are aligned in sliding engagement with the bores 232. The first ends of the legs 213 and 240 are urged together until the bearing surfaces 225 and 252 meet, causing the pins 254 to be fully received within the bores 232 and the cage system 201 to assume an overall rectangular configuration.

The intercoupled legs 210 and 211 are next inserted into an intervertebral space 202, which may be predrilled, and a bone graft is introduced in much the same manner as in the embodiments previously described. As best shown in FIG. 13, once the legs 210 and 211 are intercoupled and implanted, an exemplary driver 272 is inserted into the threaded bore 265. Using a tool (not shown) the surgeon advances the driver 272 until the tip 293 rides forwardly along the inner cam surface 234 to the junction of the two planar bearing surfaces 225 and 252. Continued advancement of the driver 272 causes the tip 293 to wedge the bearing surfaces 225 and 252 apart, withdrawing the pins 254 from the bores 232 until the tip 293 rests between the pins 254 as depicted in FIG. 14. This action simultaneously rotates the pivot 230 within the socket 264, so that the cage system 201 begins to assume a generally wedge shape when viewed from the side.

If the first chosen driver does not cause the desired angle of displacement when fully installed, then the driver 212 is removed and an alternate driver, for example 270 is selected and the process is repeated until the vertebrae 203 and 204 are supported by the cage system 201 in normal alignment.

In this manner, the modular second leg 211 includes a unitary base which supports and permits rotation of the first leg 210 about a pivot 230. The engagement of the elongate pivot 230 within the socket 264 and the pins 254 within bores 232 cooperatively prevents lateral movement of either of the legs 210 or 211 with respect to each other in response to torsional stresses.

It is to be understood that while certain forms of the present invention have been illustrated and described herein, it is not to be limited to the specific forms or arrangement of parts described and shown. In particular, any of the drivers described may be employed in any of the embodiments described, or any of an infinite variety of drivers may be employed. In addition, the legs of the invention may have a generally rectangular overall configuration as in the first described embodiment, or a more curvate configuration, as in the third embodiment described, regardless of whether the base is integral with one of the legs or comprises a separate module.

What is claimed and desired to be secured by Letters Patent is as follows:

1. An apparatus for positioning between adjacent vertebrae and comprising:
   a) a fusion cage having a first leg and a second leg, each leg having a first end, a second end and a support surface therebetween, said first ends being expandably coupled, said cage being implantable between adjacent vertebrae with said support surfaces of said legs engaging said vertebrae;
   b) said second leg including a bore and a socket for receiving said first leg second end and permitting pivotal movement within said socket; and
   c) a driver received within said bore and operable for urging said first ends apart and pivoting said second end for moving said first support surface of said fusion cage to form a selected angle.

2. The apparatus according to claim 1, wherein:
   a) said first end of said first leg includes a pair of spaced pins;
   b) said first end of said second leg includes a pair of spaced bores for receiving said pins; and
   c) said driver is received between said pins when said first ends are urged apart.

3. The apparatus according to claim 1, wherein:
   a) said first ends of said first and second legs include opposed bearing surfaces; and
   b) said bearing surfaces each include an axial groove for receiving said driver when said first ends are urged apart.

4. The apparatus according to claim 1, wherein:
   a) said bore and said driver are threaded for mating reception of said driver within said bore.

5. The apparatus according to claim 1, wherein:
   a) said driver is selected from a plurality of drivers; and
   b) each driver includes a tip sized to form said apparatus into a different predetermined angle.

6. An apparatus for positioning between adjacent vertebrae and comprising:
   a) a fusion cage having a pair of legs, each leg having a first end, a second end and a support surface therebetween, said first ends being expandably coupled, said cage being implantable between adjacent vertebrae with said support surfaces of said legs engaging said vertebrae;
   b) a base having a threaded bore and a pair of sockets for receiving said leg ends and permitting pivotal movement within said sockets; and
   c) a driver received within said bore and operable for urging said first ends apart and pivoting said second ends for moving said support surfaces of said fusion cage to form a selected angle.

7. The apparatus according to claim 6, wherein:
   a) said first end of one of said legs includes a pair of spaced pins;
   b) said first end of the other of said legs includes a pair of spaced bores for receiving said pins; and
   c) said driver is received between said pins when said first ends are urged apart.

8. The apparatus according to claim 6, wherein:
   a) said first ends of said legs each include opposed bearing surfaces; and
   b) said bearing surfaces each include an axial groove for receiving said driver when said first ends are urged apart.

9. The apparatus according to claim 6, wherein:
a) said bore and said fastener are threaded for mating reception of said fastener within said bore.

10. The apparatus according to claim 6, wherein:
a) said driver is selected from a plurality of drivers; and
b) each driver includes a tip sized to form said apparatus into a different predetermined angle.

11. An apparatus for positioning between adjacent vertebrae and comprising:
a) a pair of fusion cages for implanting in side-by-side relationship between a pair of adjacent vertebrae;
b) each fusion cage having a pair of legs, each leg having a first end, a second end and a support surface therebetween, said first ends being expandably coupled;
c) each fusion cage having a base with a threaded bore and a pair of sockets for receiving said leg ends and permitting pivotal movement with said sockets; and
d) a threaded driver received within each of said bores and operable for urging said first ends apart and moving said support surfaces of said fusion cages to form a selected angle.

12. The apparatus according to claim 11, wherein:
a) said first end of each of said first legs includes a pair of spaced pins;
b) said first end of said second leg includes a pair of spaced bores for receiving said pins; and
c) said driver is received between said pins when said first ends are urged apart.

13. The apparatus according to claim 11, wherein:
a) said first ends of said first and second legs include opposed bearing surfaces; and
b) said bearing surfaces each include an axial groove for receiving said driver when said first ends are urged apart.

14. The apparatus according to claim 11, wherein:
a) each said driver is selected from a plurality of drivers; and
b) each driver includes a tip sized to form said fusion cage into a different predetermined angle.

15. A method of positioning and stabilizing adjacent vertebrae comprising the steps of:
a) providing a fusion cage having a pair of pivotally connected legs which can be selectively anteriorly expanded by relative pivoting of said legs to form a wedge;
b) implanting said fusion cage between a pair of adjacent vertebrae such that said legs respectively engage said adjacent vertebrae;
c) providing a threaded driver adapted for expanding the anterior portion of said cage to a predetermined angle by engagement of said driver with said legs; and
d) coupling said driver with said fusion cage and expanding said fusion cage to a predetermined angle to cause alignment of the adjacent vertebrae.

16. A method of positioning and stabilizing adjacent vertebrae comprising the steps of:
a) providing a fusion cage which can be selectively anteriorly expanded to form a wedge;
b) implanting said fusion cage between a pair of adjacent vertebrae;
c) providing a threaded driver adapted for expanding the anterior portion of said implant to a predetermined angle;
d) coupling said driver with said fusion cage and expanding said fusion cage to a predetermined angle to cause alignment of the adjacent vertebrae; and
e) wherein the step of providing a driver includes the step of providing a plurality of drivers of various sizes.

17. A method of positioning and stabilizing adjacent vertebrae comprising the steps of:
a) providing a fusion cage which can be selectively anteriorly expanded to form a wedge;
b) implanting said fusion cage between a pair of adjacent vertebrae;
c) providing a plurality of threaded drivers of various sizes, each adapted for expanding the anterior portion of said implant to a predetermined angle;
d) selecting the smallest driver;
e) coupling said driver with said fusion cage and anteriorly expanding said fusion cage; and
f) removing said driver and repeating steps (d) through (f) until said fusion cage is anteriorly expanded to a predetermined angle to cause alignment of the adjacent vertebrae.

18. A spinal fusion cage comprising:
a) a base having an opening therethrough;
b) a first leg and a second leg, each leg having a first end and a second end, said first leg pivotally connected at said first end to said base such that said second end of said first leg is pivotal toward and away from said second end of said second leg;
c) a plurality of drivers, each having a tip selectively insertable through said opening in said base such that said tip engages inwardly facing surfaces of said first and second legs proximate said second ends thereof to pivot said first leg relative to said second leg to a selected angle; each of said plurality of drivers having a tip of a different size to vary the selected angle to which said first leg is pivoted relative to said second leg when said respective driver is inserted therebetween.

19. The spinal fusion cage as in claim 18 wherein:
a) said second leg is pivotally connected at said first end to said base.

20. The spinal fusion cage as in claim 18, wherein:
a) said opening through said base is threaded; and
b) each of said drivers includes a threaded shank which is removably securable within said threaded opening in said base.

* * * * *